(12) United States Patent
Dehmeshki

(10) Patent No.: US 7,460,701 B2
(45) Date of Patent: Dec. 2, 2008

(54) NODULE DETECTION

(75) Inventor: Jamshid Dehmeshki, London (GB)

(73) Assignee: Medicsight, PLC, London (GB)

( * ) Notice: Subject to any disclaimer, the term of this patent is extended or adjusted under 35 U.S.C. 154(b) by 771 days.

(21) Appl. No.: 10/868,892

(22) Filed: Jun. 17, 2004

(65) Prior Publication Data

US 2005/0259856 A1     Nov. 24, 2005

(30) Foreign Application Priority Data

May 20, 2004    (GB) ................................ 0411284.3

(51) Int. Cl.
*G06K 9/00* (2006.01)
(52) U.S. Cl. ........................ 382/131; 382/190; 382/260
(58) Field of Classification Search ........................ None
See application file for complete search history.

(56) References Cited

U.S. PATENT DOCUMENTS

| | | | |
|---|---|---|---|
| 6,125,194 | A | 9/2000 | Yeh et al. |
| 6,404,908 | B1 | 6/2002 | Schneider et al. |
| 6,882,743 | B2 | 4/2005 | Bansal et al. |
| 6,909,797 | B2 | 6/2005 | Romsdahl et al. |
| 2003/0167001 | A1 | 9/2003 | Allain et al. |
| 2004/0086161 | A1 | 5/2004 | Sivaramakrishna et al. |
| 2005/0207630 | A1* | 9/2005 | Chan et al. .................. 382/131 |
| 2007/0140541 | A1* | 6/2007 | Bae et al. .................... 382/131 |

FOREIGN PATENT DOCUMENTS

| | | |
|---|---|---|
| EP | 1 755 457 | 2/2007 |
| WO | WO 01/54065 A1 | 7/2001 |
| WO | WO 02/085211 A2 | 10/2002 |
| WO | WO 02/103065 A2 | 12/2002 |
| WO | WO 03/024184 A2 | 3/2003 |
| WO | WO 03/070102 A2 | 8/2003 |

OTHER PUBLICATIONS

"Computer-Aided Diagnosis: A Neural-Network-Based Approach to Lung Nodule Detection" by Penedo et al. Medical Imaging, IEEE Transactions on vol. 17, Issue 6, Dec. 1998 pp. 872-880.*

"Shape Based Region Growing Using Derivatives of 3D Medical Images: Application to Semi-Automated Detection of Pulmonary Nodules" by Dehmeshki et al., Image Processing, 2003. ICIP 2003. Proceedings. 2003 International Conference on vol. 1, Sep. 14-17, 2003 pp. I-1085-8 vol. 1.*

(Continued)

*Primary Examiner*—Charles Kim
(74) *Attorney, Agent, or Firm*—Sterne, Kessler, Goldstein & Fox, PLLC.

(57) ABSTRACT

A method of detecting a nodule in a three-dimensional scan image comprises calculating a three-dimensional sphericity index for each point in the scan image (310-330), applying a high sphericity threshold to the sphericity index (340) to obtain a candidate nodule region, and then performing region-growing (350) from the candidate region using a relaxed sphericity threshold to determine an extended region including less spherical parts connected to the candidate region. Optionally, spherical filtering may be applied to the image by matching the spherical filter to the extended region.

23 Claims, 20 Drawing Sheets

OTHER PUBLICATIONS

Armato et al., "Three-Dimensional Approach to Lung Nodule Detection in Helicat CT" Proceedings of the SPIE, Bellingham, VA, US, vol. 3661, Feb. 22, 1999, pp. 553-559.

Kanazawa et al., "Computer Aided Diagnosis for Pulmonary Nodules Based on Helical CT Images" Computerized Medical Imaging and Graphics, Pergamon Press, New York, NY, vol. 22, No. 2, Mar. 1998, pp. 157-167.

International Search Report, dated Sep. 5, 2005, for PCT Application No. PCT/GB2005/001837, 2 pages.

Examination Report, dated Apr. 16, 2008, for British Application No. 0411284.3, 3 pages.

Search Report, dated Nov. 25, 2004, for British Application No. 0411284.3, 1 page.

Dehmeshki, et al., "Automated detection of lung nodules in CT images using shape-based genetic algorithm," Computerized Medical Imaging and Graphics 31, pp. 408-417 (2007).

Ye, et al., "Efficient Computer-Aided Detection of Ground-Glass Opacity Nodules in Thoracic CT Images," IEEE Engineering in Medicine and Biology Conference (2007).

* cited by examiner

NODULE DETECTION

RELATED APPLICATIONS

This application claims the benefit of the filing date of GB Patent Application No. 0411284.3, filed May 20, 2004, which is incorporated herein by reference in its entirety.

FIELD OF THE INVENTION

The present invention relates to a method of detecting nodules in computed tomography (CT) images, and particularly but not exclusively for detecting nodules in CT images of the lung. The method may be implemented using a computer, and the invention encompasses software and apparatus for carrying out the method.

BACKGROUND OF THE INVENTION

The mortality rate for lung cancer is higher than that for other kinds of cancers around the world. Detection of suspicious lesions in the early stages of cancer can be considered the most effective way to improve survival. Nodule detection is one of the more challenging tasks in medical imaging. Nodules may be difficult to detect on CT scans because of low contrast, small size, or location of the nodule within an area of complicated anatomy.

Computer-assisted techniques have been proposed to identify regions of interest containing a nodule within a CT scan image, to segment the nodule from surrounding objects such as blood vessels or the lung wall, to calculate physical characteristics of the nodule, and/or to provide an automated diagnosis of the nodule. Fully automated techniques perform all of these steps without intervention by a radiologist, but one or more of these steps may require input from the radiologist, in which case the method may be described as semi-automated.

Many lung nodules are approximately spherical, and various techniques have been proposed to identify spherical structures within a CT scan image. For example, the Nodule-Enhanced Viewing algorithm from Siemens AG is believed to perform thresholding on a three-dimensional (3D) CT scan to identify voxels having an intensity between predetermined maximum and minimum values. The identified voxels are grouped into connected objects, and objects which are approximately spherical are highlighted.

U.S. 2003/0099391 discloses a method for automatically segmenting a lung nodule by dynamic programming and expectation maximization (EM), using a deformable circular model to estimate the contour of the nodule in each two-dimensional (2D) slice of the scan image, and fitting a three-dimension (3D) surface to the contours.

U.S. 2003/0167001 discloses a method for automatically segmenting a CT image to identify regions of interest and to detect nodules within the regions of interest, in which a sphere is modeled within the region of interest, and points within the sphere are identified as belonging to a nodule, while a morphological test is applied to regions outside the sphere to determine whether they belong to the nodule.

Although many nodules are approximately spherical, the non-spherical aspects of a nodule may be most important for calculating physical characteristics and for performing diagnosis. A spherical model may be useful to segment nodules from surrounding objects, but if the result is to incorrectly identify the nodule as a sphere and to discard non-spherical portions of the nodule, the characteristics of the nodule may also be incorrectly identified.

SUMMARY OF THE INVENTION

According to an embodiment of the present invention, there is provided a method of detecting a nodule in a three-dimensional scan image, comprising calculating a sphericity index for each point in the scan image relative to surrounding points of similar intensity, applying a high sphericity threshold to the sphericity index to obtain a candidate nodule region, and then performing region-growing from the candidate region using a relaxed sphericity threshold to identify an extended region including less spherical parts connected to the candidate region. The extended region may be provided for display and/or for subsequent processing to calculate physical characteristics and/or to perform automatic diagnosis. In an embodiment, diagnosis may be performed by a radiologist on the basis of the enhanced image.

The present inventor has realized that even non-spherical nodules generally include an approximately spherical region of a particular density: for example, a dense, spherical core may be surrounded by a slightly less dense, less spherical region that nevertheless forms part of the nodule. If a thresholding technique is applied to such a nodule, then only the shape of the outer, non-spherical region will be detected, and will be rejected as a candidate nodule because it is not sufficiently spherical. If the threshold is set between the density of the inner, spherical region and the outer, non-spherical region, then only the inner region will be detected and the outer region will be discarded. In contrast, embodiments of the present invention may allow such non-spherical nodules to be detected in their entirety.

Preferably, the sphericity index is calculated from the first and second partial derivatives of the smoothed image in each direction at each point, and by calculating principal curvatures at each voxel. Equal curvatures in each direction give a high sphericity index. This method is less computationally intensive than explicitly generating iso-intensity surfaces for the image and then deriving the sphericity index from those iso-intensity surfaces.

Preferably, the partial derivatives are calculated on a smoothed image. The smoothing function may involve the convolution of a smoothing function with the image. The smoothing may be applied at the same time as the partial derivatives are calculated, by convolving the scan image with the partial derivatives of the smoothing function.

As an additional step, the extended region may be enhanced in the scan image by applying a spherical filter. The spherical filter may be fitted to the extended region by convolving the filter with the image, or a map of the sphericity of the image, and adjusting the filter until a maximum convolution value is achieved. The spherical filter may include a positive weighting in an inner region and a negative weighting in an outer region. The enhanced image may be output for display, and alternatively or additionally be used as input for subsequent processing stages.

BRIEF DESCRIPTION OF THE DRAWINGS

FIGS. 7a, 7b to 11a, 11b show original images and images with spherical enhancement of five different real scans.

FIGS. 15a, 15b to 20a, 20b show original images and spherically filtered images respectively of six different real scans.

DETAILED DESCRIPTION OF THE EMBODIMENTS

CT Image

Each embodiment is performed on series of CT image slices obtained from a CT scan of the chest area of a human or animal patient. Each slice is a 2-dimensional digital grey-scale image of the x-ray absorption of the scanned area. The properties of the slice depend on the CT scanner used; for example, a high-resolution multi-slice CT scanner may produce images with a resolution of 0.5-0.6 mm/pixel in the x and y directions (i.e. in the plane of the slice). Each pixel may have 32-bit grayscale resolution. The intensity value of each pixel is normally expressed in Hounsfield units (HU). Sequential slices may be separated by a constant distance along the z direction (i.e. the scan separation axis); for example, by a distance of between 0.75-2.5 mm. Hence, the scan image is a three-dimensional (3D) grey scale image, with an overall size depending on the area and number of slices scanned.

The present invention is not restricted to any specific scanning technique, and is applicable to electron beam computed tomography (EBCT), multi-detector or spiral scans or any technique that produces as output a 3D image, representing for example X-ray absorption or density.

Figure 1:
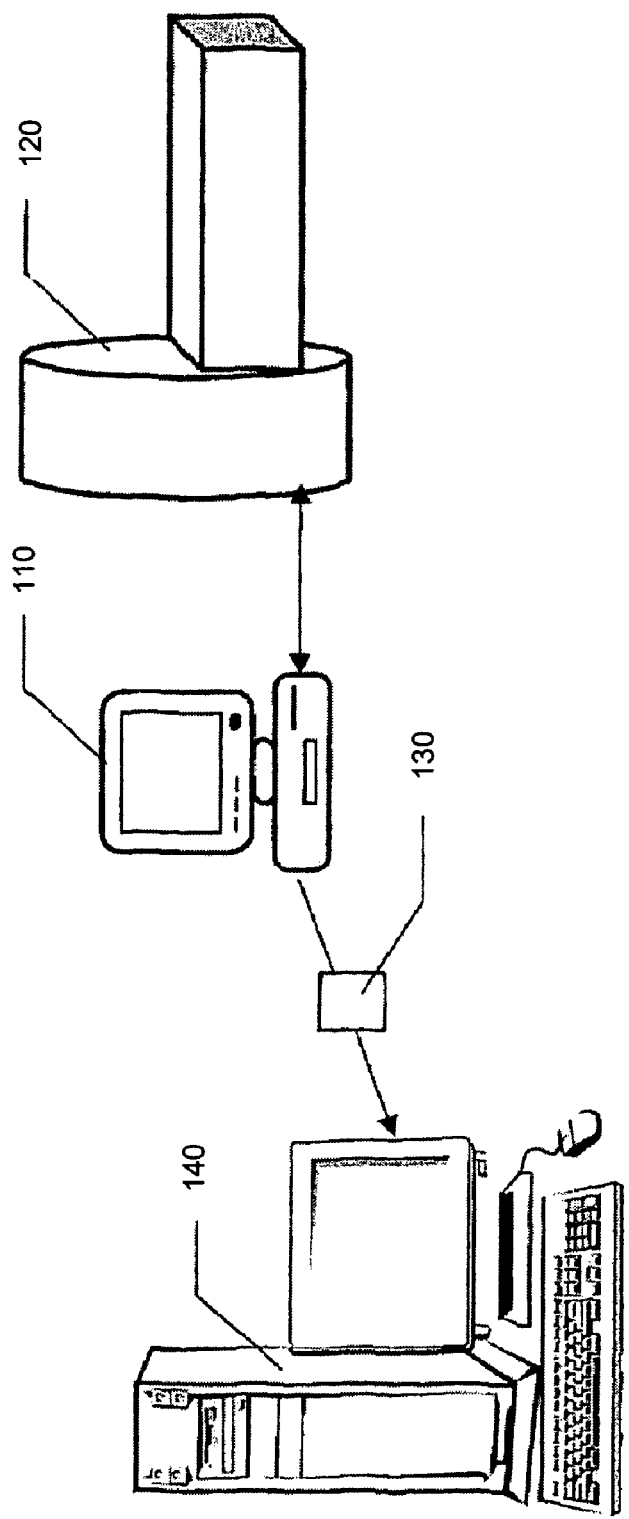
FIG. 1 is a schematic diagram showing a CT scanner and a remote computer for processing image data from the scanner according to an embodiment of the present invention.

As shown in FIG. 1, the scan image is created by a computer 110 which receives scan data from a scanner 120 and constructs the scan image. The scan image is saved as an electronic file or a series of files which are stored on a storage medium 130, such as a fixed or removable disc. The scan image may be processed by the computer 110 to identify and display lung nodules, or the scan image may be transferred to another computer 140 which runs software for processing the image as described below. The image processing software may be stored on a carrier, such as a removable disc, or downloaded over a network.

Figure 2:
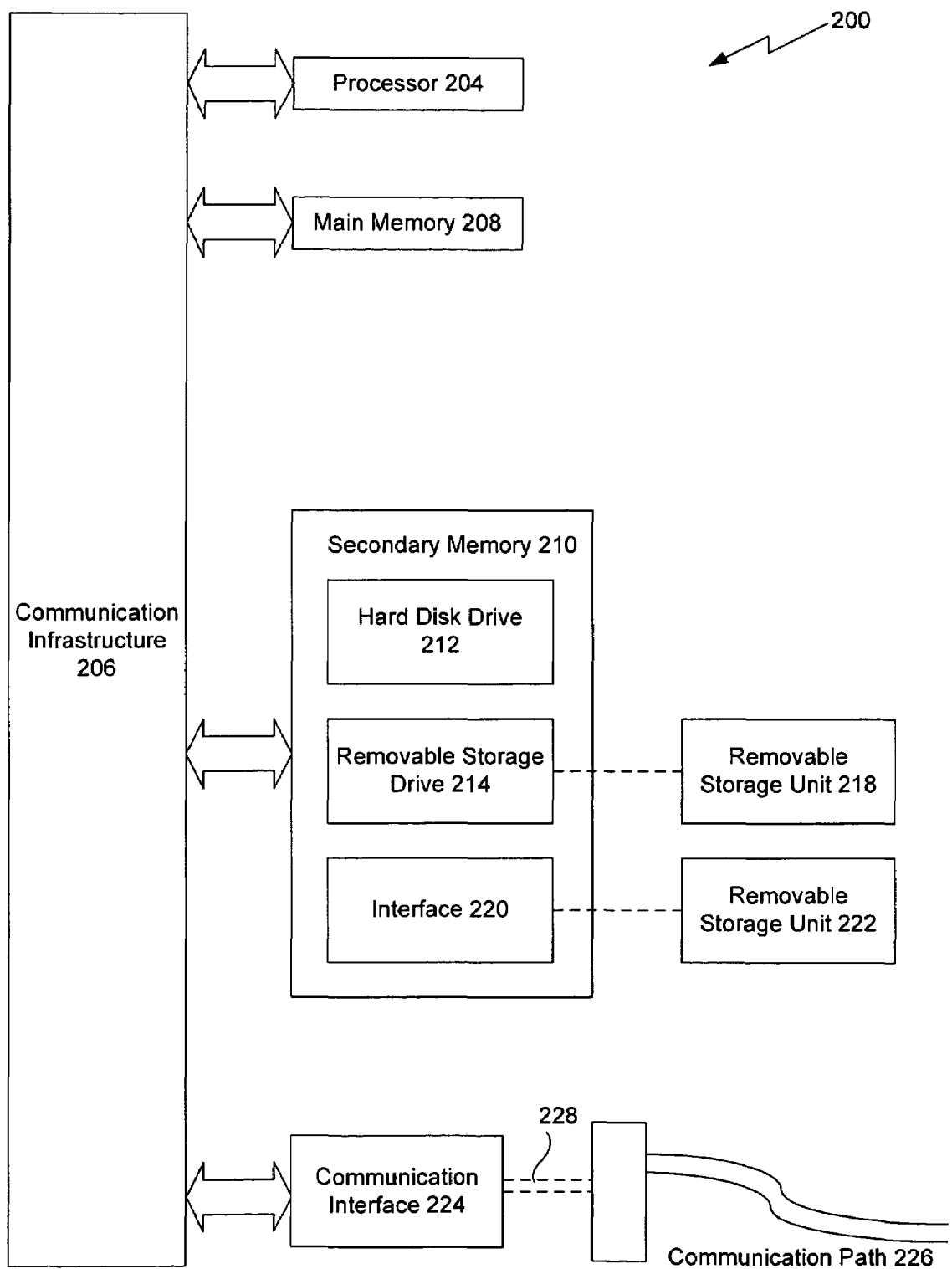
FIG. 2 is an example computer system according to an embodiment of the present invention.

FIG. 2 illustrates an example computer system 200, in which the present invention can be implemented as programmable code. Various embodiments of the invention are described in terms of this example computer system 200. After reading this description, it will become apparent to a person skilled in the art how to implement the invention using other computer systems and/or computer architectures.

The computer system 200 includes one or more processors, such as processor 204. Processor 204 can be a special purpose or a general purpose digital signal processor. The processor 204 is connected to a communication infrastructure 206 (for example, a bus or network). Various software implementations are described in terms of this exemplary computer system. After reading this description, it will become apparent to a person skilled in the art how to implement the invention using other computer systems and/or computer architectures.

Computer system 200 also includes a main memory 208, preferably random access memory (RAM), and may also include a secondary memory 210. The secondary memory 210 may include, for example, a hard disk drive 212 and/or a removable storage drive 214, representing a floppy disk drive, a magnetic tape drive, an optical disk drive, etc. The removable storage drive 214 reads from and/or writes to a removable storage unit 218 in a well known manner. Removable storage unit 218, represents a floppy disk, magnetic tape, optical disk, etc. which is read by and written to by removable storage drive 214. As will be appreciated, the removable storage unit 218 includes a computer usable storage medium having stored therein computer software and/or data.

In alternative implementations, secondary memory 210 may include other similar means for allowing computer programs or other instructions to be loaded into computer system 200. Such means may include, for example, a removable storage unit 222 and an interface 220. Examples of such means may include a program cartridge and cartridge interface (such as that found in video game devices), a removable memory chip (such as an EPROM, or PROM) and associated socket, and other removable storage units 222 and interfaces 220 which allow software and data to be transferred from the removable storage unit 222 to computer system 200.

Computer system 200 may also include a communication interface 224. Communication interface 224 allows software and data to be transferred between computer system 200 and external devices. Examples of communication interface 224 may include a modem, a network interface (such as an Ethernet card), a communication port, a Personal Computer Memory Card International Association (PCMCIA) slot and card, etc. Software and data transferred via communication interface 224 are in the form of signals 228 which may be electronic, electromagnetic, optical, or other signals capable of being received by communication interface 224. These signals 228 are provided to communication interface 224 via a communication path 226. Communication path 226 carries signals 228 and may be implemented using wire or cable, fiber optics, a phone line, a cellular phone link, a radio frequency link, or any other suitable communication channel. For instance, the communication path 226 may be implemented using a combination of channels.

In this document, the terms "computer program medium" and "computer usable medium" are used generally to refer to media such as removable storage drive 214, a hard disk installed in hard disk drive 212, and signals 228. These computer program products are means for providing software to computer system 200.

Computer programs (also called computer control logic) are stored in main memory 208 and/or secondary memory 210. Computer programs may also be received via communication interface 224. Such computer programs, when executed, enable the computer system 200 to implement the present invention as discussed herein. Accordingly, such computer programs represent controllers of the computer system 200. Where the invention is implemented using software, the software may be stored in a computer program product and loaded into computer system 200 using removable storage drive 214, hard disk drive 212, or communication interface 224, to provide some examples.

Calculation of High Sphericity Areas

Figure 3:
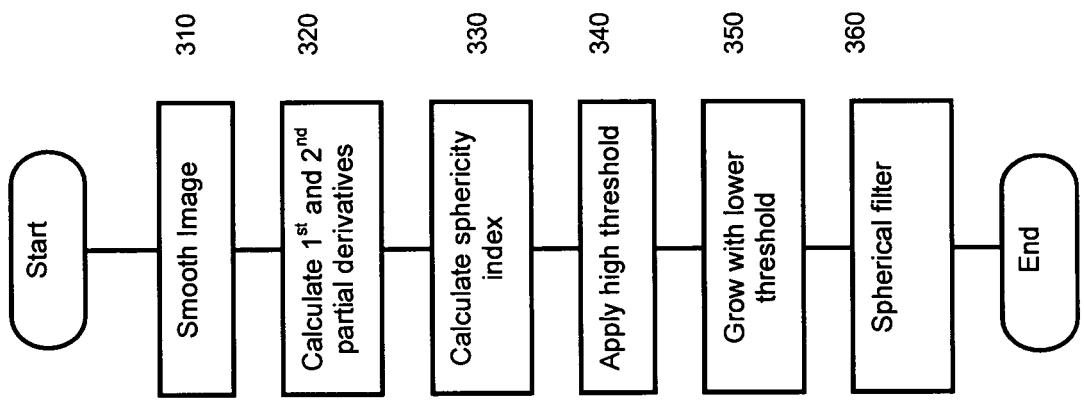
FIG. 3 is a flowchart of an algorithm according to an embodiment of the present invention.

An embodiment comprises image-processing software for detecting nodules in a three-dimensional CT scan image of a lung. The embodiment uses an algorithm comprising three principle steps. First, a 3D sphericity index (SI) is calculated for each volume element within the 3D image (voxel); secondly, based on the computed sphericity index map, a high SI threshold is used to determine a spherical region; then, a relaxed SI threshold is applied and the 3D connectivity of voxels above the relaxed threshold to the spherical region is calculated to determine the extent of the nodule. The detailed process is described below, with reference to the flowchart of FIG. 3.

Shape feature calculation and sphericity index map construction

For a 3D image with the intensity of I(p) at a point p=(x,y,z), an iso-surface P at the level a in a 3-D space $\Re^3$ is given by $$P \equiv \{p=(x,y,z) \in \Re^3; I(p)=a\}$$

Figure 4:
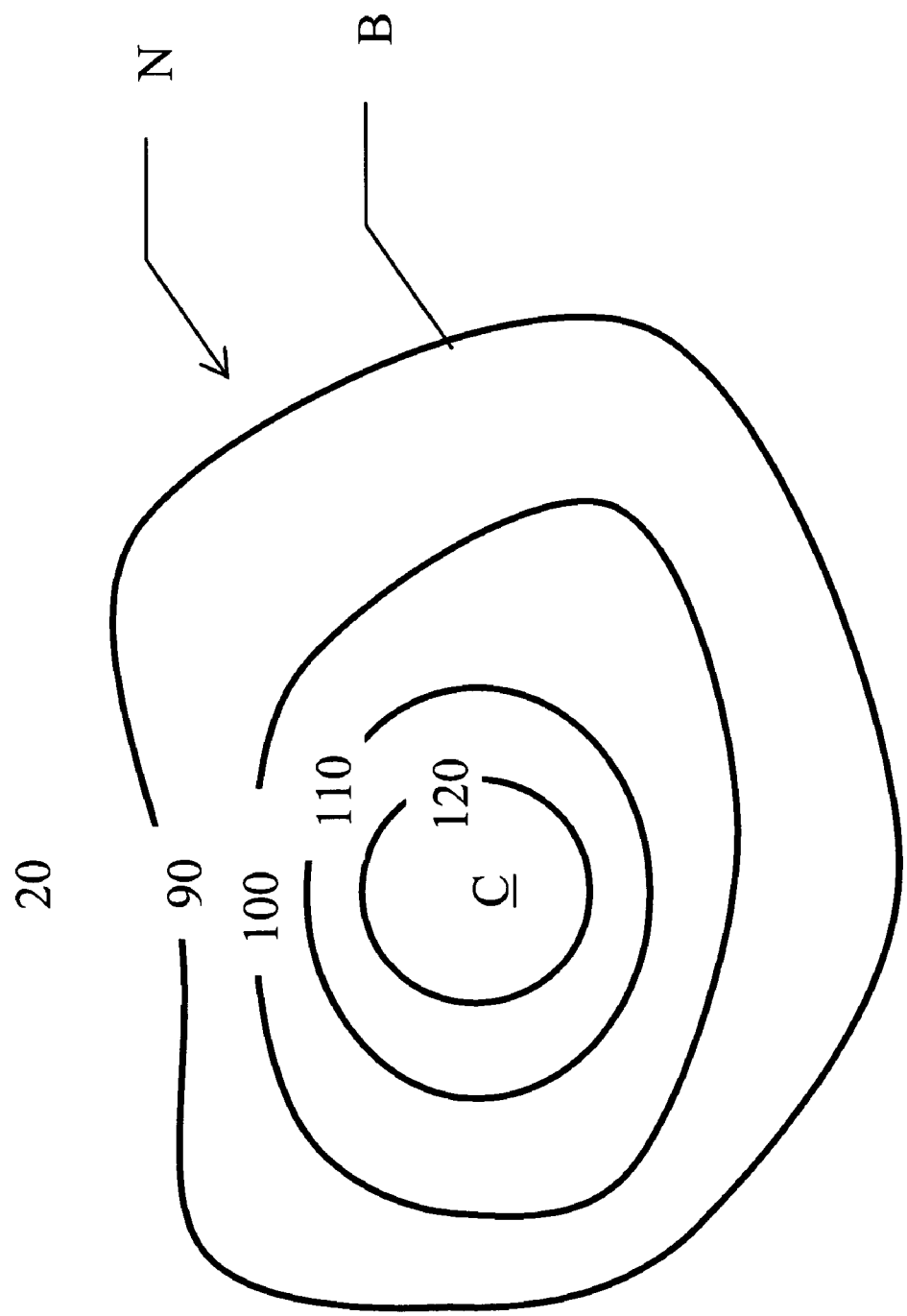
FIG. 4 is a diagram of a nodule showing iso-intensity contours.
Figure 5C:
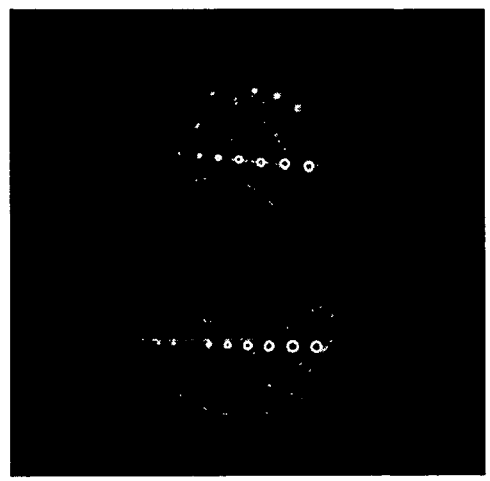
FIGS. 5a-5c and 6a-6c show original images and images with spherical enhancement of two different lung phantoms.
Figure 5B:
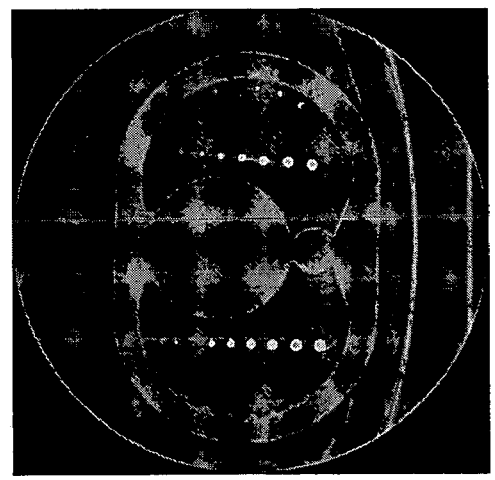
Figure 5A:
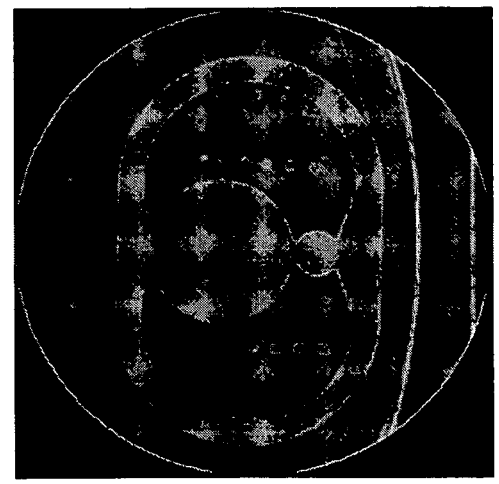
Figure 6C:
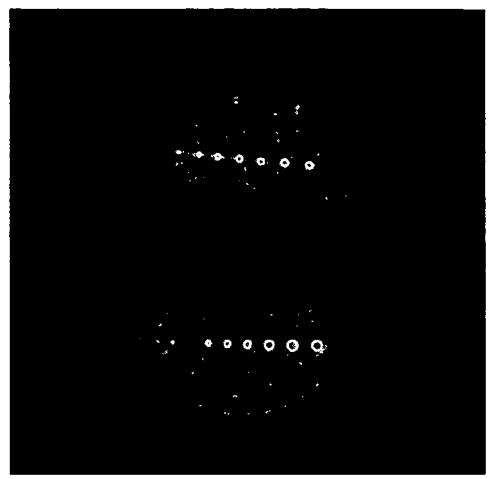
Figure 6B:
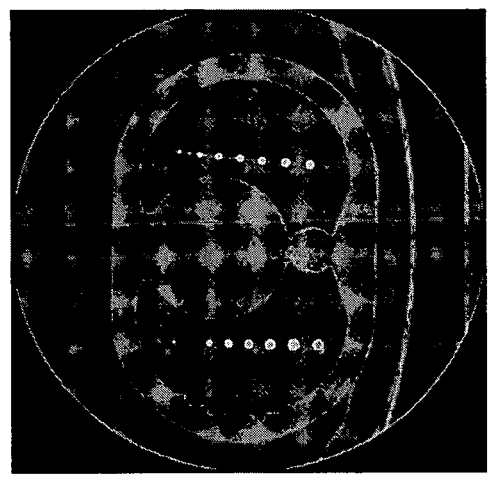
Figure 6A:
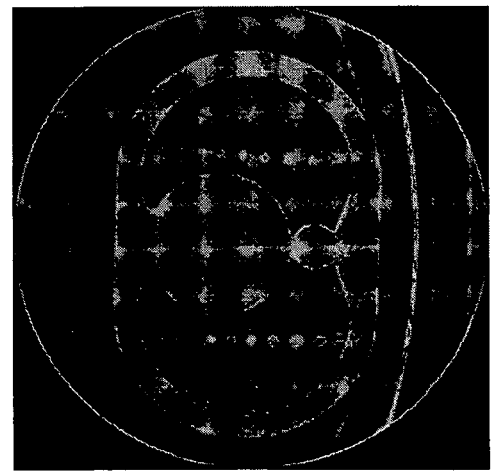
Figure 7B:
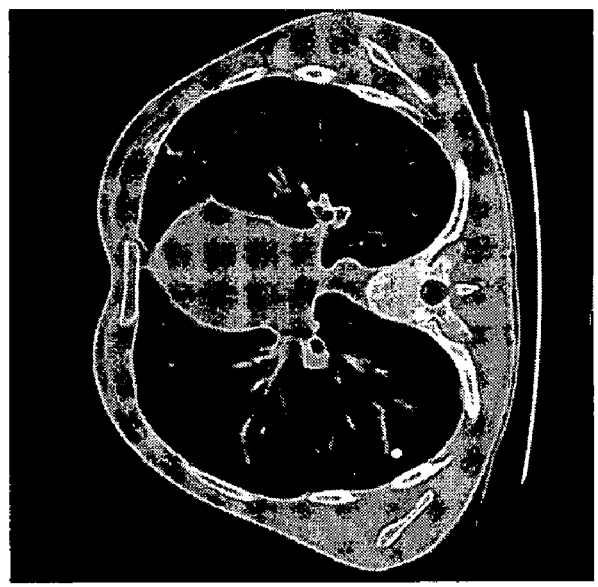
Figure 7A:
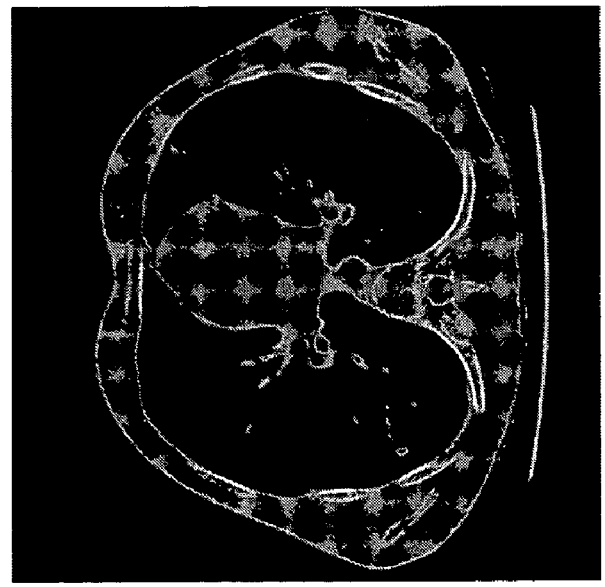
Figure 8B:
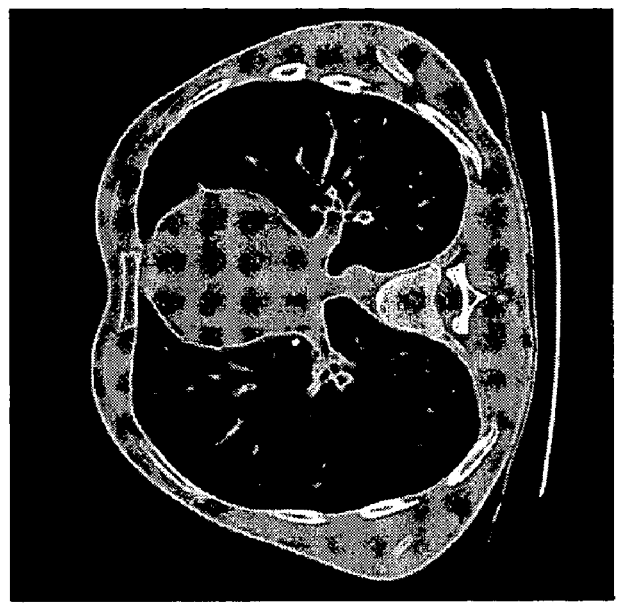
Figure 8A:
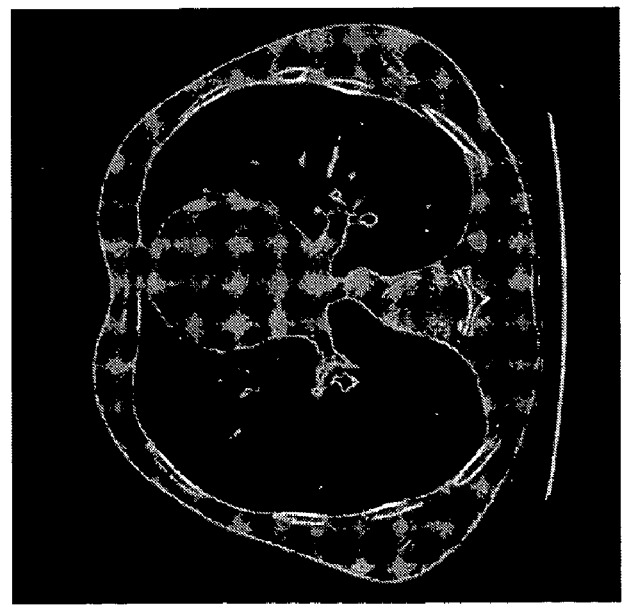
Figure 9B:
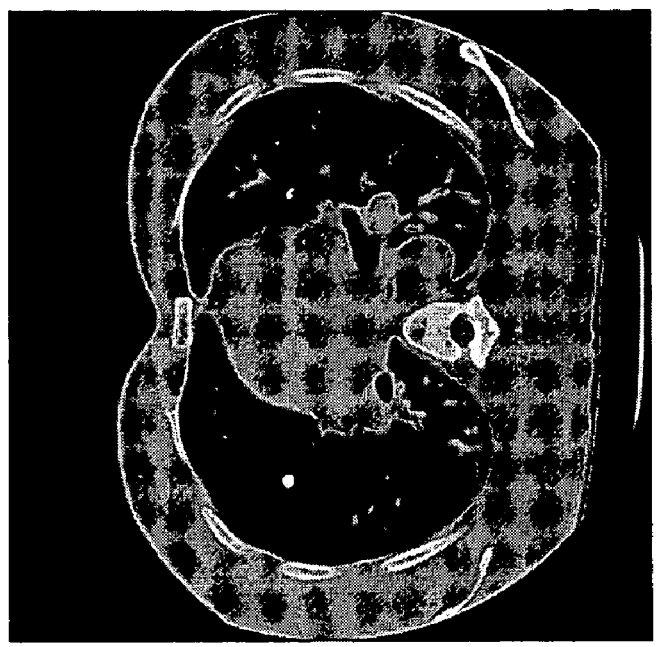
Figure 9A:
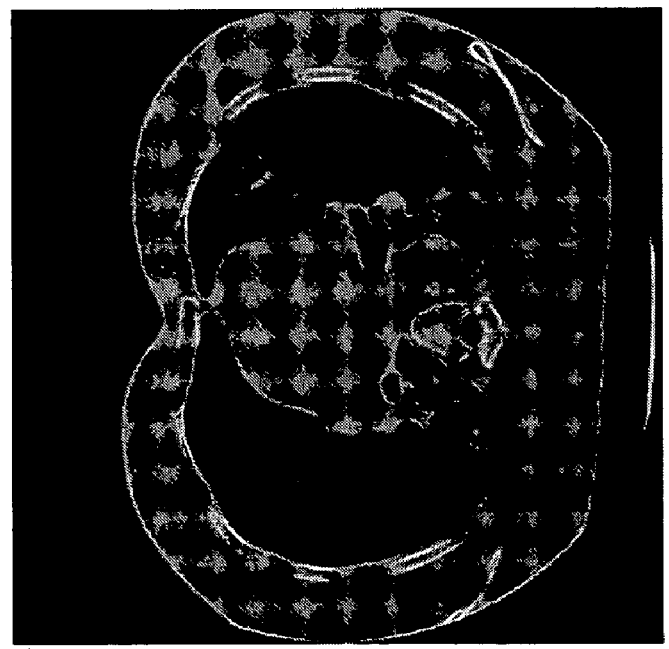
Figure 10B:
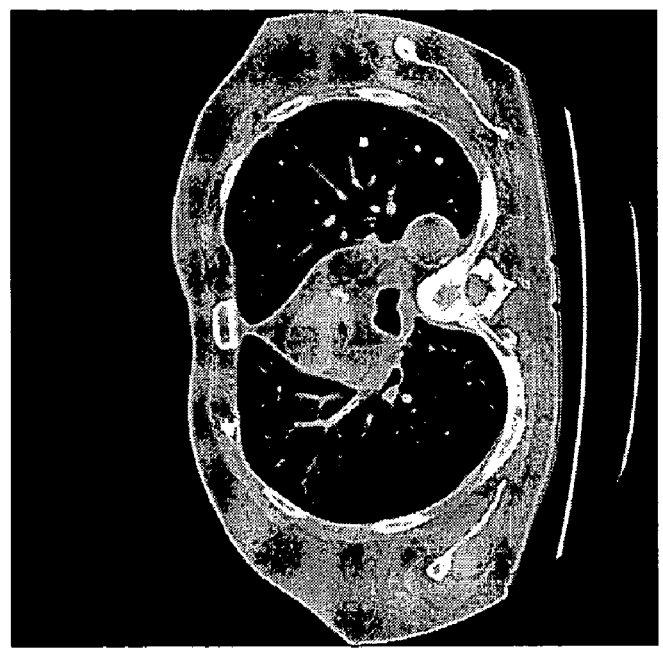
Figure 10A:
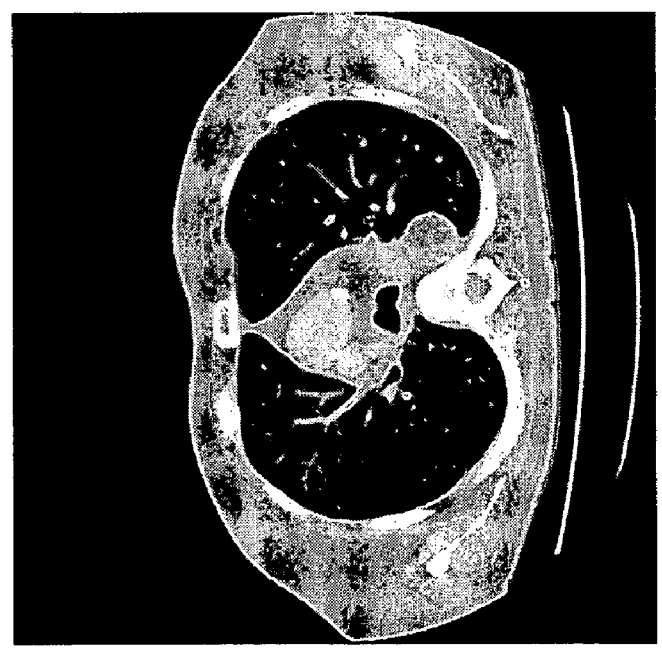
Figure 11B:
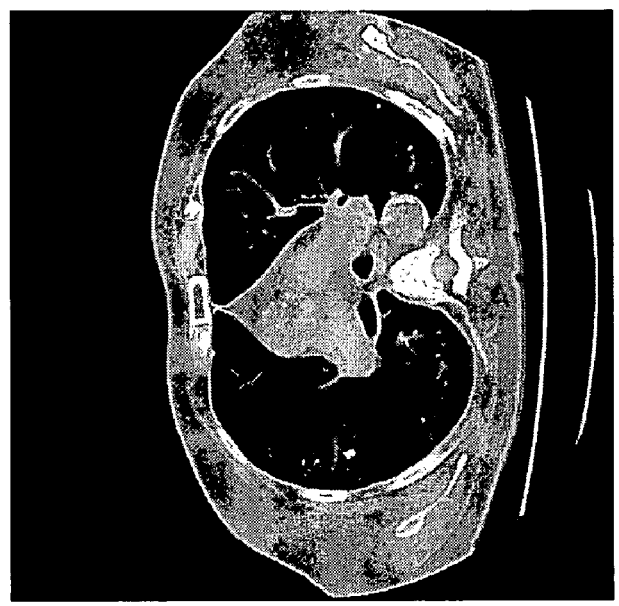
Figure 11A:
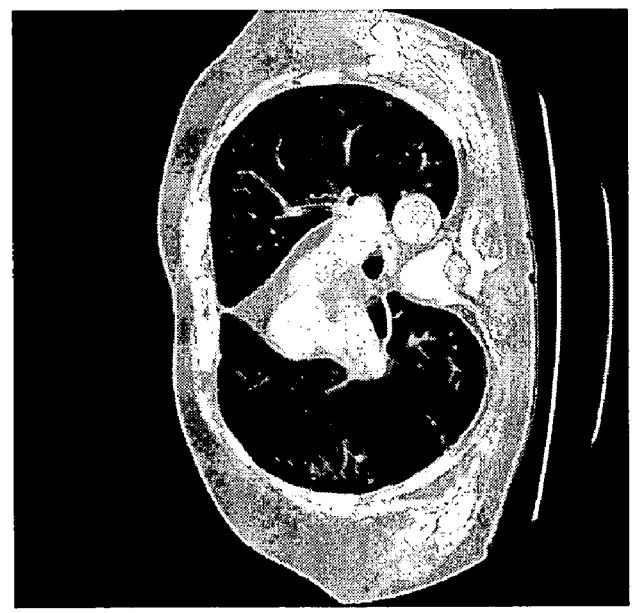

FIG. 4 shows iso-intensity contours of a single slice of a sample nodule N, with intensity expressed in Hounsfield units (HU). In this case, the background intensity is 20 HU, while the outer boundary of the nodule is at approximately 90 HU, rising to over 120 HU at the core. Note that the core C is spherical (circular in this slice), while the outer boundary B is less spherical.

To compute the typical surface features, such as the principal curvature, a traditional approach is to fit a parametric surface model to the 3D image and then to compute the differential characteristics of the surface in the local coordinate system. Because it is very computationally intensive to explicitly generate an iso-surface, the differential characteristics of the surface in this embodiment are calculated directly from the 3D image without explicitly defining an iso-surface. The main steps are described below.

The 3D image I(x,y,z) is convolved with the Gaussian function g(x,y,z) to generate a smoothed digital 3D image (step 310):

$$h(x,y,z)=I(x,y,z)*g(x,y,z) \qquad (1)$$

where $$g(x, y, z) = \frac{1}{\sigma\sqrt{2\pi}} e^{-\frac{[(x-\mu_x)^2+(y-\mu_y)^2+(z-\mu_z)^2]}{2\sigma^2}}$$

and * is a convolution operator.

Next, we compute the first and second partial derivatives of the smoothed 3D image h(x,y,z) (step 320).

The first partial derivate of h(x,y,z) in the x direction is defined as:

$$h_x = \frac{dh}{dx} = \frac{d(I(x, y, z)*g(x, y, z))}{dx} \qquad (2)$$

Based on the properties of the convolution operator, we have:

$$\frac{d(I(x, y, z)*g(x, y, z))}{dx} = \frac{dI(x, y, z))}{dx} * g(x, y, z)$$

$$= I(x, y, z) * \frac{dg(x, y, z)}{dx}$$

So, the equation (1) can be rewritten as:

$$h_x = I(x, y, z) * \frac{dg(x, y, z)}{dx} \qquad (3)$$

Using the same method we can define $h_y$, $h_z$ which are the first partial derivatives in the y and z direction, respectively, and also the second partial derivatives $h_{xx}$, $h_{yy}$, $h_{zz}$, $h_{xy}$, $h_{xz}$, $h_{yz}$. For example, $h_{xy}$ which is the second partial derivative in the x and y direction is defined as:

$$h_{xy} = \frac{d^2 h(x, y, z)}{dxy} \qquad (4)$$

$$= \frac{d(I(x, y, z)*g(x, y, z))}{dxy}$$

$$= I(x, y, z) * \frac{d^2 g(x, y, z)}{dxy}$$

Note that according to the above definition of the partial derivatives of the smoothed 3D image h(x,y,z) (e.g. equation 3 and equation 4), in the implementation process, both stages of the smoothing and calculating partial derivatives can be combined into one step, namely, the partial derivatives of the smoothed 3D images can be obtained by convoluting the raw 3D image I(x,y,z) with the high order Gaussian filters.

Next, we compute the shape features using the first and second order partial derivatives (step 330).

Compute Gaussian (K(p)) and mean (H(p)) curvatures:

$$K = \frac{1}{|h|^2} \sum_{(i,j,k)=Perm(x,y,z)} \{h_i(h_{jj}h_{kk} - h_{hk}^2) + 2h_jh_k(h_{ik}h_{ij} - h_{ii}h_{jk})\}$$

$$H = \frac{1}{|h|^{3/2}} \sum_{(i,j,k)=Perm(x,y,z)} \{-h_i^2(h_{jj} + h_{kk}) + 2h_jh_kh_{jk}\}, h = \sum_{i=x,y,z} h_i^2$$

Principal curvatures (k1(p), k2(p)) at each voxel p:

$$k_1(p)=H(p)+\sqrt{(H^2(p)-K(p))}$$

$$k_2(p)=H(p)-\sqrt{(H^2(p)-K(p))}$$

Sphericity index:

$$SI(p) = \frac{1}{2} - \frac{1}{\pi}\arctan\frac{k_1(p)+k_2(p)}{k_1(p)-k_2(p)}$$

The sphericity index SI(p) characterizes the topological shape of the volume in the vicinity of the voxel p, whereas the volumetric curvature represents the magnitude of the effective curvature. Both quantities are based on two principal curvatures defined as above. The sphericity index is a function of the difference between a maximum curvature and a minimum curvature of an iso-surface at each point. If the curvature is equal in all directions, the iso-surface is a section of the surface of a sphere and the sphericity index is 1. If the iso-surface is a section of the surface of a cylinder, the sphericity index is 0.75. It is important to exclude cylindrical shapes as these are normally blood vessels.

High Sphericity Index Region for Sphere-Like Object Seed

A high threshold (e.g. 0.90) is applied to the sphericity index SI(p) (step 340), so that a set of foreground voxels is obtained for which SI(p) is above the threshold, and the foreground voxels are grouped together into connected regions. This grouping together may be done by region growing from an ungrouped foreground voxel, so as iteratively to add neighboring foreground voxels to the group until no neighboring foreground voxels exist. The process is then repeated from another ungrouped foreground voxel to define another group, until all foreground voxels belong to a group. Neighbors may be added in each of the three spatial dimensions, so that the region grows in three dimensions. The result is one or more highly spherical regions within the image. In the sample nodule N, this highly spherical region might extend only to the core C.

The high threshold may be fixed by the software, or may be variable by the user, for example within the range 0.8 to 1.0.

Region Growing Based on a Relaxed Sphericity Index Threshold

Each of the highly spherical regions is used as an object seed for three-dimensional region growing. To each object seed, neighboring voxels above a relaxed shape-index threshold (e.g. SI(p)>0.80) are added using a three-dimensional region growing technique (step 350). The region-growing technique is applied iteratively to the region, so that neighboring voxels above the relaxed sphericity index threshold are added to the region and new neighbors are then added if they are above the relaxed threshold, and the process continues until there are no new neighbors above the relaxed threshold. The result is one or more detected regions including connected areas of lower sphericity. In the example of FIG. 4, the detected region may grow as far as the boundary B.

The relaxed threshold may be fixed by the software, or may be variable by the user, for example within the range 0.75 to 0.85, but must in any case be lower than the high threshold.

The detected regions may be highlighted for display in the original image, or may be displayed without the original image. The detected regions may be viewed by the radiologist as an aid to diagnosis, or may be provided as input to further processing steps to calculate physical characteristics and/or to perform automatic diagnosis.

Results

Lung Phantom Data

FIGS. 5*a*-5*c* and 6*a*-6*c* show the results of the spherical object enhancement on two different phantoms, with a) an original scan image, b) the scan image with the detected regions enhanced, and c) the detected regions without the original image.

Real Lung Data

FIGS. 7*a*, 7*b* to 11*a*, 11*b* show single slice CT scans with a) the original scan image and b) the scan image with the detected regions enhanced.

Conclusion

The proposed method has been implemented and tested on both phantom and clinical lung images. It demonstrates high performance in detecting objects such as lung nodules.

Spherical Filtering

An optional spherical enhancement step may be applied to the detected regions, to enhance lung nodules in a CT lung image by using spherical filtering (step 360).

The spherical filtering process is based on image convolution with a spheroid kernel. The filter kernel has two distinct regions: a positively biased spherical inner region that has a diameter of the filter size, and a negatively biased outer shell region that has an inner diameter that is the filter size and an outer diameter that is less than twice the inner diameter, and is preferably set so that the volumes of the inner and outer shell regions are equal.

Figure 12:
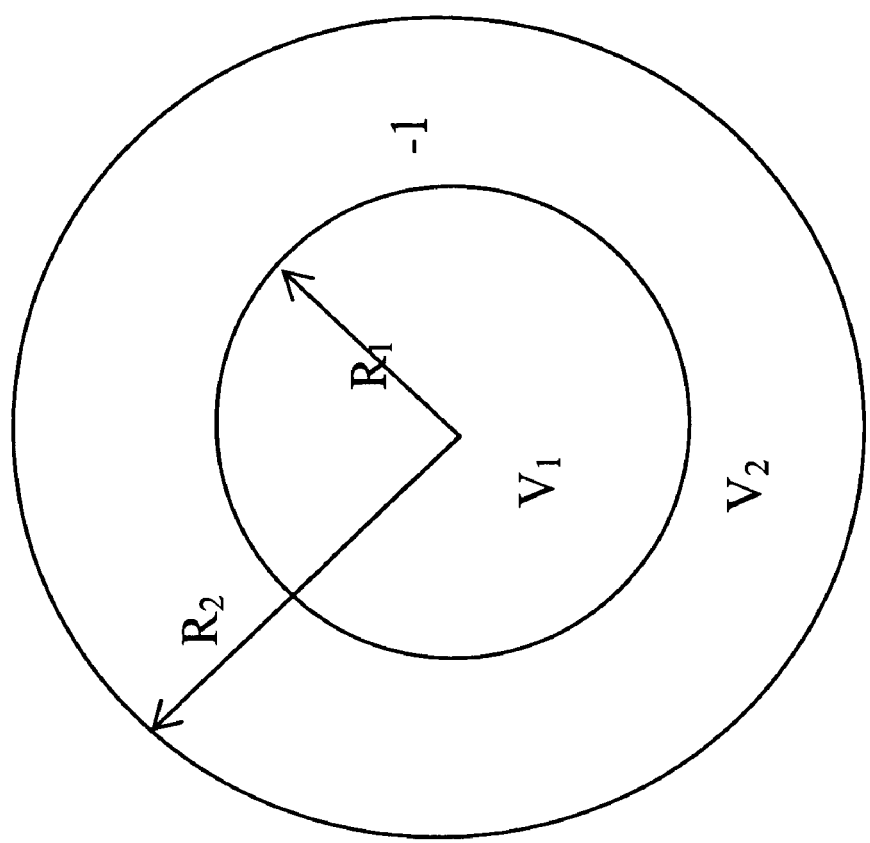
FIG. 12 illustrates a spherical filter according to an embodiment of the present invention.

With reference to FIG. 12, suppose the inner and outer radii are $R_1$ and $R_2$ respectively. The condition for inner region volume and outer region volume to be the same is $V_1=V_2$, where $$V_1 = \frac{4}{3}\pi R_1^2 \text{ and}$$

$$V_2 = \frac{4}{3}\pi R_2^2 - \frac{4}{3}\pi R_1^2$$

therefore $R_2 = 1.26 R_1$

The filter kernel defines a volumetric weighting function such that points within the inner region are positively weighted, while points in the outer region are negatively weighted. In a simple example, the positive weight is +1 and the negative weight is −1. The volumetric weighting function is then convolved with the scan image data, and the convolution is summed to calculate a convolution strength. In the simple example, this means that the convolution strength is the sum of the intensities in the outer region subtracted from the sum of the intensities in the inner region.

Figure 13:
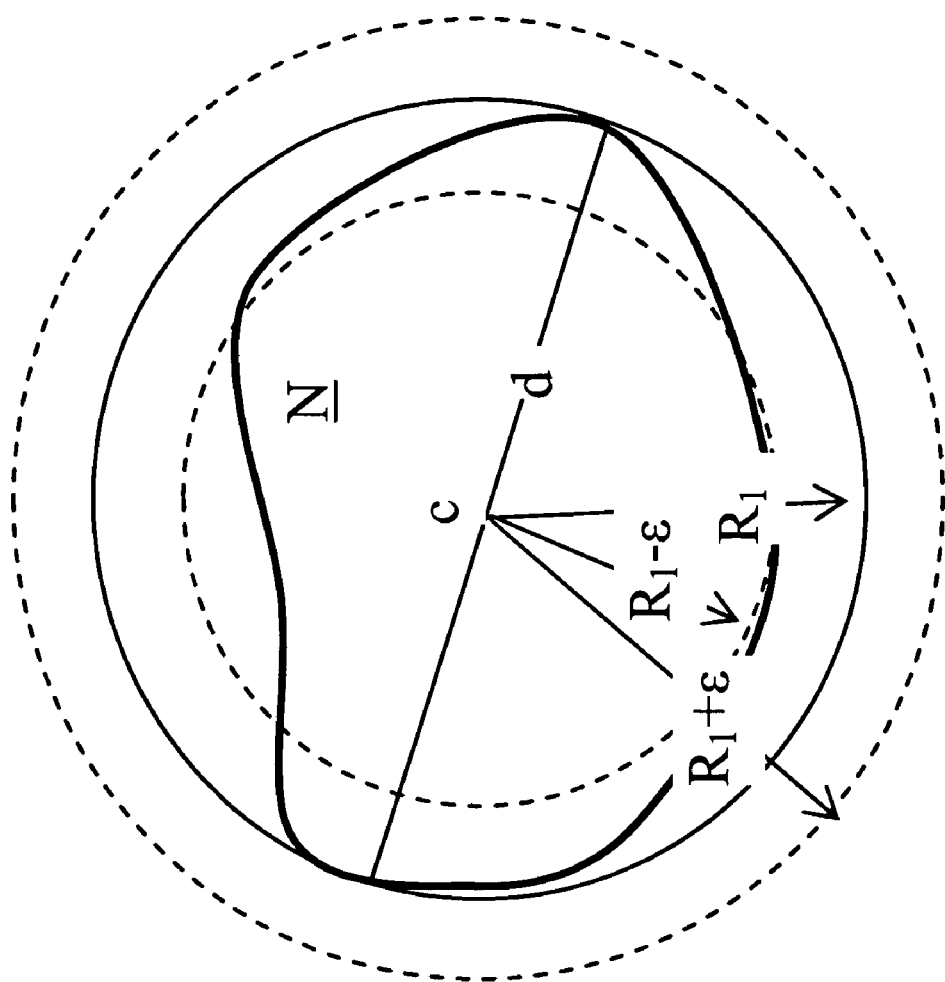
FIG. 13 illustrates the variation in radius of a spherical filter according to an embodiment of the present invention.

With reference to FIG. 13, for each detected region, the maximum diameter d of the detected region is set as the initial diameter of the spherical inner region of the filter kernel, and the centre c of the filter kernel is set as the midpoint of the diameter d. The outer diameter of the outer shell region is set so that the volumes of the inner and outer regions are the same.

The radius $R_1$ is then varied stepwise through a range $R_1 \pm \epsilon$, where $\epsilon$ is a small difference, such as 20% of $R_1$. For each stepwise variation, $R_2$ is varied correspondingly so that the inner and outer regions have the same volume, and the convolution strength is calculated. The maximum convolution strength is recorded, and the spherical filter with the corresponding value of $R_1$ is used to enhance the image. For example, the image may be convolved with the spherical filter and the convoluted image may be output for display.

In an alternative embodiment, the spherical filtering may be applied to the sphericity map rather than to the original image.

Experimental Results

Figure 14B:
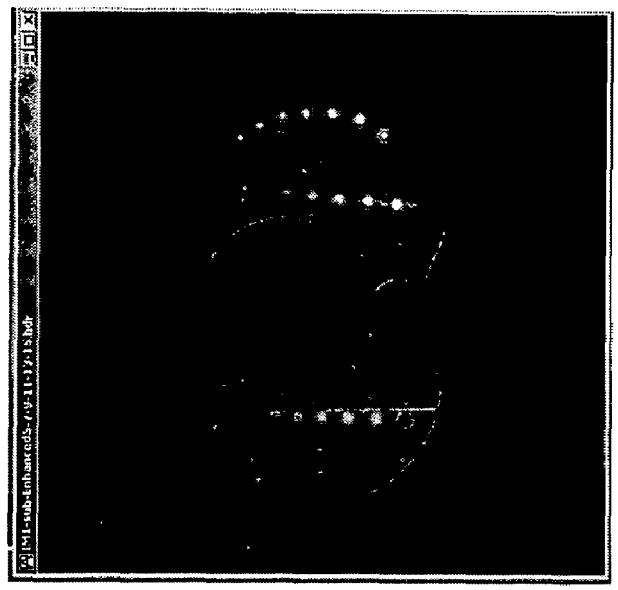
FIGS. 14a and 14b show an original image and a spherically filtered image of a lung phantom.
Figure 14A:
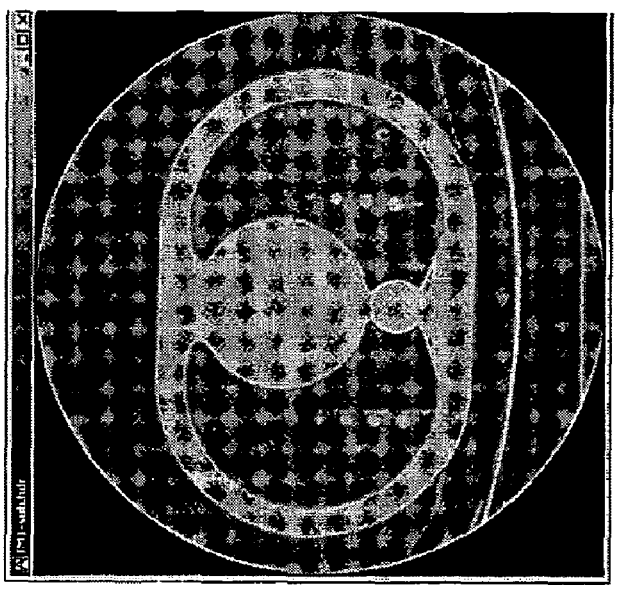
Figure 15B:
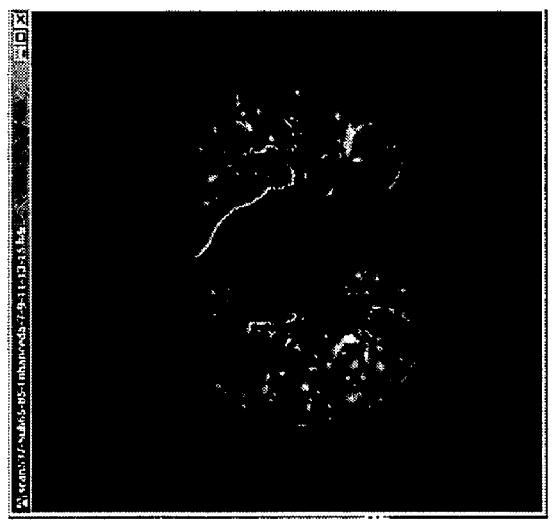
Figure 15A:
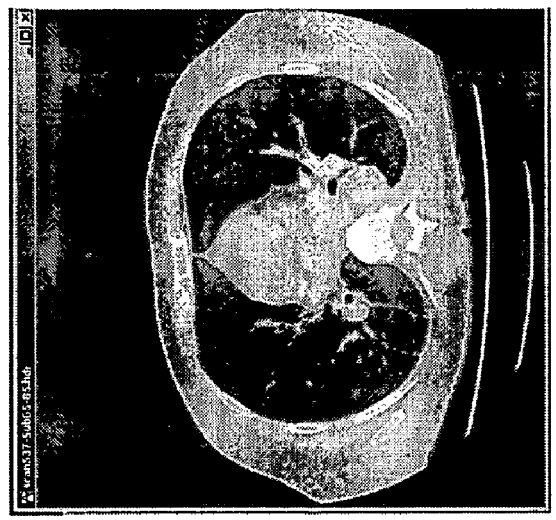
Figure 16B:
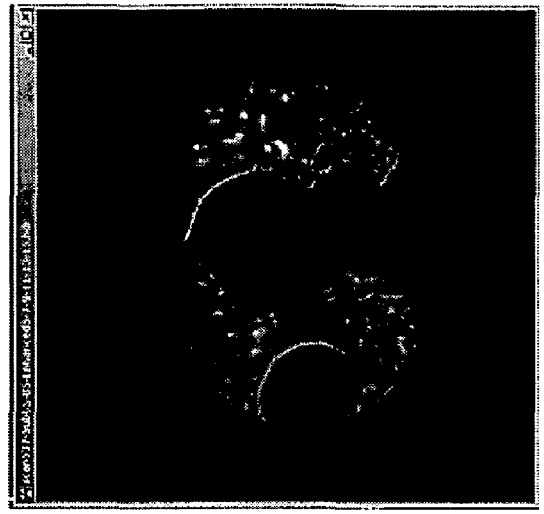
Figure 16A:
Figure 17B:
Figure 17A:
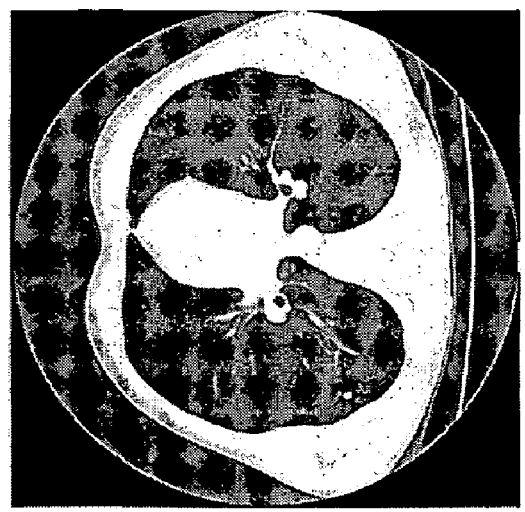
Figure 18B:
Figure 18A:
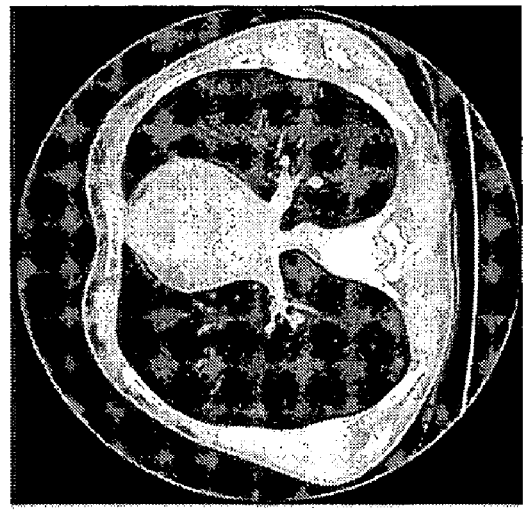
Figure 19B:
Figure 19A:
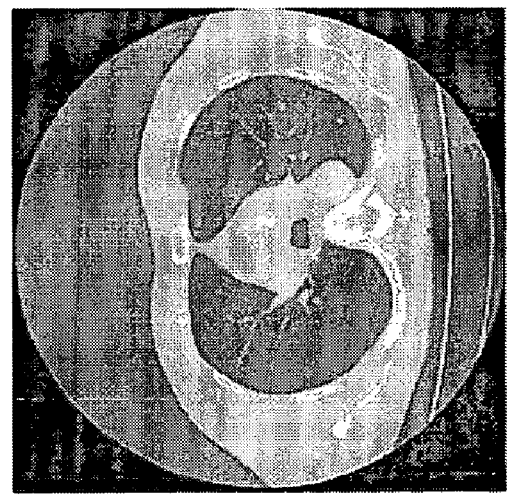
Figure 20B:
Figure 20A:
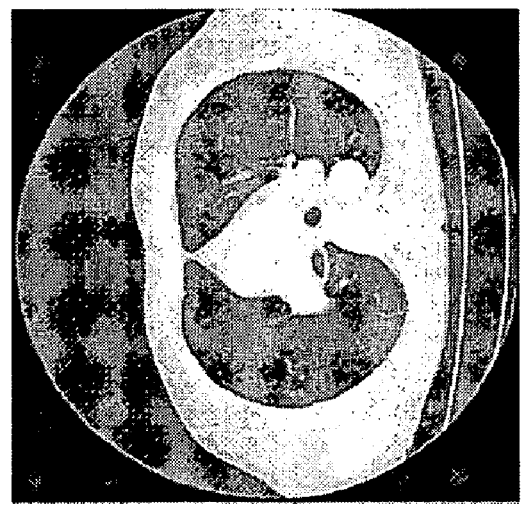

In the following tests the kernel diameters used are:
5, 7, 9, 11, 13, 15 pixels
4.9, 6.3, 7.7, 9.1, 10.5 millimeters The maximum convolution results (strength) and the size of the kernel are recorded and saved in the output image. FIGS. 14*a* and 14*b* show a) an original and b) spherically filtered image of a phantom, while FIGS. 15*a*, 15*b* to 20*a*, 20*b* show a) original and b) spherically filtered images from actual CT lung scans.

CONCLUSION

The spheroid filtering method has been implemented and tested on both phantom and clinical lung images, with good results where the nodules were generally spherical in shape.

Alternative Embodiments

The embodiments above are described by way of example, and are not intended to limit the scope of the invention. Various alternatives may be envisaged which nevertheless fall within the scope of the claims.

What is claimed is:

1. A method of identifying a nodule in a computed tomography scan image of at least part of a lung, comprising:
   a. calculating a sphericity index map of a plurality of points within the image;

b. identifying a region of high sphericity within the image by identifying connected ones of said points having a sphericity index above a predetermined high sphericity index threshold as belonging to said region;

c. performing three-dimensional region growing from said region by adding to said region ones of said points having a sphericity index above a relaxed sphericity index threshold, said relaxed sphericity index threshold being lower than said high sphericity index threshold, to form an extended region; and d. outputting, said extended region as an identified nodule.

2. The method of claim 1, wherein the sphericity index indicates the variation in curvature of an iso-intensity surface in the region around each said point.

3. The method of claim 2, wherein the sphericity index is calculated from a partial derivative of intensity around each said point.

4. The method of claim 3, wherein the sphericity index is calculated from the first and second partial derivatives of intensity of said image in three dimensions.

5. The method of claim 1, wherein the sphericity index map is calculated on a smoothed said image.

6. The method of claim 1, further including performing filtering around said extended region using a spherical filter.

7. A method of identifying a nodule in a computed tomography scan image of at least part of a lung, comprising:
a. identifying a region of high sphericity within the image;
b. extending the region to include connected points of lower sphericity;
c. performing filtering around the extended region using a spherical filter comprising an inner spherical region of positive weight and an outer spherical region of negative weight, to form a filtered extended region; and
d. outputting said filtered extended region as an identified nodule.

8. The method of claim 7, wherein the inner and outer spherical regions have substantially equal volumes.

9. The method of claim 7, wherein the inner spherical region has a diameter substantially equal to the diameter of the extended region.

10. The method of claim 7, wherein the filtering step comprises convolving the inner and outer spherical regions with said image.

11. The method of claim 10, further comprising varying a diameter of the inner spherical region so as to determine a maximum strength of said convolution, and applying spherical filtering corresponding to the maximum convolution strength to the scan image to generate a spherically enhanced output image.

12. A method of identifying a nodule in a computed tomography scan image of at least part of a lung, comprising:
a. calculating a sphericity index map of a plurality of points within the image;
b. identifying a region of high sphericity within the image by identifying connected ones of said points having a sphericity index above a predetermined high sphericity index threshold as belonging to said region;
c. extending the region to include connected points of lower sphericity, to form an extended region;
d. performing filtering around the extended region using a spherical filter comprising an inner spherical region of positive weight and an outer spherical region of negative weight, wherein the filtering comprises convolving the inner and outer spherical regions with the sphericity index map, to form a filtered extended region; and
e. outputting the filtered extended region as an identified nodule.

13. The method of claim 12, further comprising varying a diameter of the inner spherical region so as to determine a maximum strength of said convolution, and applying spherical filtering corresponding to the maximum convolution strength to the sphericity index map to generate a spherically enhanced output image.

14. Apparatus for identifying a nodule in a computed tomography scan image of at least part of a lung, comprising:
means for identifying a region of high sphericity within the image, including means for calculating a sphericity index map of a plurality of points within the image, and for identifying connected points having a sphericity index above a predetermined high sphericity index threshold as belonging to said region;
means for extending the region by performing three-dimensional region growing from said region to add connected points having a sphericity index above a relaxed sphericity index threshold, said relaxed sphericity index threshold being lower than said high sphericity index threshold, to form an extended region; and
means for outputting the extended region as an identified nodule.

15. The apparatus of claim 14, wherein the sphericity index indicates the variation in curvature of an iso-intensity surface in the region around each said point.

16. The apparatus of claim 15, wherein the sphericity index is calculated from a partial derivative of intensity around each said point.

17. The apparatus of claim 16, wherein the sphericity index is calculated from the first and second partial derivatives of intensity of said image in three dimensions.

18. The apparatus of claim 14, wherein the sphericity index map is calculated on a smoothed said image.

19. Apparatus for identifying a nodule in a computed tomography scan image of at least part of a lung, comprising:
means for calculating a sphericity index map of a plurality of points within the image;
means for identifying a region of high sphericity within the image by identifying connected ones of said points having a sphericity index above a predetermined high sphericity index threshold as belonging to said region;
means for performing three-dimensional region growing from said region to add connected points of lower sphericity, to form an extended region;
means for performing filtering around the extended region using a spherical filter comprising an inner spherical region of positive weight and an outer spherical region of negative weight, wherein the filtering comprises convolving the inner and outer spherical regions with the sphericity index map, to form a filtered extended region; and
means for outputting the filtered extended region as an identified nodule.

20. A computer readable storage medium having recorded thereon program code to perform the following processes for identifying a nodule in a computed tomography scan image of at least part of a lung:
a. calculating a sphericity index map of a plurality of points within the image;
b. identifying a connected region of high sphericity index within the image by identifying connected ones of said points having a sphericity index above a predetermined high sphericity index threshold as belonging to said connected region;
c. performing three-dimensional region growing from said connected region to add connected points of lower sphericity, to form an extended region;

d. performing filtering around the extended region using a spherical filter comprising an inner spherical region of positive weight and an outer spherical region of negative weight, wherein the filtering comprises convolving the inner and outer spherical regions with the sphericity index map, to form a filtered extended region; and e. outputting the filtered extended region as an identified nodule.

21. An article comprising a computer readable storage medium for storing instructions to enable a processor-based system to:

a. calculate a sphericity index map of a plurality of points within a computed tomography scan image of at least part of a lung;
   b. identify a region of high sphericity within the image by identifying connected ones of said points having a sphericity index above a predetermined high sphericity index threshold as belonging to said region;
   c. extend the region to include connected points of lower sphericity, to form an extended region;
   d. perform filtering around the extended region using a spherical filter comprising an inner spherical region of positive weight and an outer spherical region of negative weight, wherein the filtering comprises convolving the inner and outer spherical regions with the sphericity index map, to form a filtered extended region; and
   e. output the filtered extended region as an identified nodule.

22. A computer readable storage medium having recorded thereon program code to perform the following processes for identifying a nodule in a computed tomography scan image of at least part of a lung:

a. calculating a sphericity index map of a plurality of points within the image;
   b. identifying a region of high sphericity within the image by identifying connected ones of said points having a sphericity index above a predetermined high sphericity index threshold as belonging to said region;
   c. performing three-dimensional region growing from said region by adding to said region ones of said points having a sphericity index above a relaxed sphericity index threshold, said relaxed sphericity index threshold being lower than said high sphericity index threshold, to form an extended region; and
   d. outputting said extended region as an identified nodule.

23. An article comprising a computer readable storage medium for storing instructions to enable a processor-based system to:

a. calculate a sphericity index map of a plurality of points within a computed tomography scan image of at least part of a lung;
   b. identify a region of high sphericity within the image by identifying connected ones of said points having a sphericity index above a predetermined high sphericity index threshold as belonging to said region;
   c. perform three-dimensional region growing from said region by adding to said region ones of said points having a sphericity index above a relaxed sphericity index threshold, said relaxed sphericity index threshold being lower than said high sphericity index threshold, to form an extended region; and
   d. output said extended region as an identified nodule.

* * * * *